(12) United States Patent
Bourang et al.

(10) Patent No.: US 12,239,802 B2
(45) Date of Patent: Mar. 4, 2025

(54) CATHETER MANAGEMENT DEVICE

(71) Applicant: Advanced Bifurcation Systems Inc., Livermore, CA (US)

(72) Inventors: Ashur Bourang, Turlock, CA (US); Henry Bourang, Turlock, CA (US)

(73) Assignee: Advanced Bifurcation Systems Inc., Livermore, CA (US)

( * ) Notice: Subject to any disclaimer, the term of this patent is extended or adjusted under 35 U.S.C. 154(b) by 0 days.

(21) Appl. No.: 17/715,630

(22) Filed: Apr. 7, 2022

(65) Prior Publication Data

US 2022/0226612 A1    Jul. 21, 2022

Related U.S. Application Data

(63) Continuation of application No. 16/997,119, filed on Aug. 19, 2020, now Pat. No. 11,324,925.

(60) Provisional application No. 62/889,667, filed on Aug. 21, 2019.

(51) Int. Cl.
*A61M 25/02* (2006.01)
*A61M 25/01* (2006.01)

(52) U.S. Cl.
CPC ..... *A61M 25/02* (2013.01); *A61M 2025/0177* (2013.01); *A61M 2025/028* (2013.01)

(58) Field of Classification Search
CPC .......... A61M 25/02; A61M 2025/0177; A61M 2025/028
USPC ........................................................ 604/523
See application file for complete search history.

(56) References Cited

U.S. PATENT DOCUMENTS

| | | | |
|---|---|---|---|
| 4,405,312 A | 9/1983 | Gross et al. | |
| 5,389,082 A | 2/1995 | Baugues et al. | |
| 7,172,162 B2 * | 2/2007 | Mizukoshi | B60H 1/00557 |
| | | | 248/65 |
| 7,457,506 B1 | 11/2008 | Osborne, II | |
| 8,672,276 B2 * | 3/2014 | Fukumoto | F16L 3/2235 |
| | | | 248/316.1 |
| 9,400,431 B2 * | 7/2016 | Wu | F16L 3/10 |
| 11,324,925 B2 | 5/2022 | Bourang et al. | |
| 2003/0229313 A1 | 12/2003 | Bierman | |
| 2007/0276336 A1 | 11/2007 | Bierman et al. | |
| 2010/0006738 A1 | 1/2010 | Teirstein | |

(Continued)

FOREIGN PATENT DOCUMENTS

| | | |
|---|---|---|
| CN | 1279622 A | 1/2001 |
| CN | 1696559 A | 11/2005 |

(Continued)

OTHER PUBLICATIONS

"U.S. Appl. No. 16/997,119, Corrected Notice of Allowability mailed Feb. 24, 2022", 5 pgs.

(Continued)

*Primary Examiner* — Phillip A Gray
(74) *Attorney, Agent, or Firm* — Schwegman Lundberg & Woessner, P.A.

(57) ABSTRACT

An elongate shaft management device has an upper plate and a lower plate. The lower plate has at least one groove that is sized to receive the elongate shaft. The at least one groove in the lower plate cooperates with the upper plate to capture the elongate shaft and prevent movement of the elongate shaft. The upper plate is releasably coupled to the lower plate to provide access to the elongate shaft and allow it to be manipulated.

15 Claims, 11 Drawing Sheets

(56) References Cited

U.S. PATENT DOCUMENTS

| | | | |
|---|---|---|---|
| 2012/0136314 A1 | 5/2012 | Ciccone et al. | |
| 2012/0172846 A1* | 7/2012 | Nakamoto | A61M 25/002 |
| | | | 604/533 |
| 2013/0079722 A1 | 3/2013 | Makino et al. | |
| 2013/0206623 A1* | 8/2013 | Spaargaren | A61M 25/002 |
| | | | 206/363 |
| 2017/0333680 A1 | 11/2017 | Bentley et al. | |
| 2018/0280662 A1 | 10/2018 | Abu-Sultaneh et al. | |
| 2019/0217076 A1 | 7/2019 | O'Neil | |
| 2021/0052856 A1 | 2/2021 | Bourang et al. | |

FOREIGN PATENT DOCUMENTS

| | | |
|---|---|---|
| CN | 103028184 A | 4/2013 |
| CN | 106267527 A | 1/2017 |
| CN | 114269415 A | 4/2022 |
| EP | 0567029 | 10/1993 |
| KR | 20110070462 | 6/2011 |
| WO | WO-2018186615 A1 | 10/2018 |
| WO | WO-2021034909 A2 | 2/2021 |
| WO | WO-2021034909 A3 | 2/2021 |

OTHER PUBLICATIONS

"U.S. Appl. No. 16/997,119, Non Final Office Action mailed Oct. 28, 2021", 10 pgs.
"Application Serial No. 16/997,119, Notice of Allowance mailed Feb. 11, 2022", 8 pgs.
"Application Serial No. 16/997,119, Response filed Jan. 12, 2022 to Non Final Office Action mailed Oct. 28, 2021", 11 pgs.
"International Application Serial No. PCT/US2020/046953, International Preliminary Report on Patentability mailed Mar. 3, 2022", 11 pgs.
"International Application Serial No. PCT/US2020/046953, International Search Report mailed Feb. 16, 2021", 2 pgs.
"International Application Serial No. PCT/US2020/046953, Written Opinion mailed Feb. 16, 2021", 9 pgs.
"Chinese Application Serial No. 202080058739.1, Office Action mailed Jun. 20, 2023", W/English Translation, 29 pgs.
"European Application Serial No. 20855500.3, Response to Communication pursuant to Rules 161(2) and 162 EPC filed Sep. 29, 2022", 12 pgs.
"European Application Serial No. 20855500.3, Extended European Search Report mailed Sep. 19, 2023", 6 pgs.
"Chinese Application Serial No. 202080058739.1, Response filed Nov. 3, 2023 to Office Action mailed Jun. 20, 2023", w English claims, 19 pgs.
"Chinese Application Serial No. 202080058739.1, Decision of Rejection mailed Nov. 28, 2023", w/ English Translation, 20 pgs.
"European Application Serial No. 20855500.3, Response filed Feb. 20, 2024 to Extended European Search Report mailed Sep. 19, 2023", 52 pgs.
"Chinese Application Serial No. 202080058739.1, Response filed Mar. 13, 2024 to Decision of Rejection mailed Nov. 28, 2023" 45 pgs.
"European Application Serial No. 20855500.3, Response filed Sep. 10, 2024 to Communication Pursuant to Article 94(3) EPC mailed May 10, 2024", 11 pgs.
"European Application Serial No. 20855500.3, Communication Pursuant to Article 94(3) EPC mailed May 10, 2024", 5 pgs.

* cited by examiner

CATHETER MANAGEMENT DEVICE

CLAIM OF PRIORITY

The present application is a continuation of U.S. patent application Ser. No. 16/997,119 filed on Aug. 19, 2020 now U.S. Pat. No. 11,324,925, which is a non-provisional of, and claims the benefit of U.S. Provisional Patent Application No. 62/889,667 filed on Aug. 21, 2010; the entire contents of each of which is incorporated herein by reference.

BACKGROUND

Many therapeutic and diagnostic procedures are performed using catheters and/or guidewires to access target areas of the body using minimally invasive techniques. For example, blockages in the heart are treated using angioplasty catheters or stent delivery catheters thereby avoiding open heart surgery. Guidewires are often used to facilitate advancement of the diagnostic or therapeutic catheter to the target area, and often multiple catheters or multiple guidewires may be used during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Many therapeutic and diagnostic procedures are performed using catheters and/or guidewires to access target areas of the body using minimally invasive techniques. For example, blockages in the heart are treated using angioplasty catheters or stent delivery catheters thereby avoiding open heart surgery. Guidewires are often used to facilitate advancement of the diagnostic or therapeutic catheter to the target area, and often multiple catheters and guidewires may be used during the procedure. A physician must keep track of each guidewire and catheter to ensure that they are not mixed up, and the multiple catheter shafts or guidewires must be prevented from entangling with one another so that manipulation and control of the catheters and guidewires is still possible. At least some of the examples of catheter and guidewire management devices disclosed herein will address at least some of these challenges.

Figure 1:
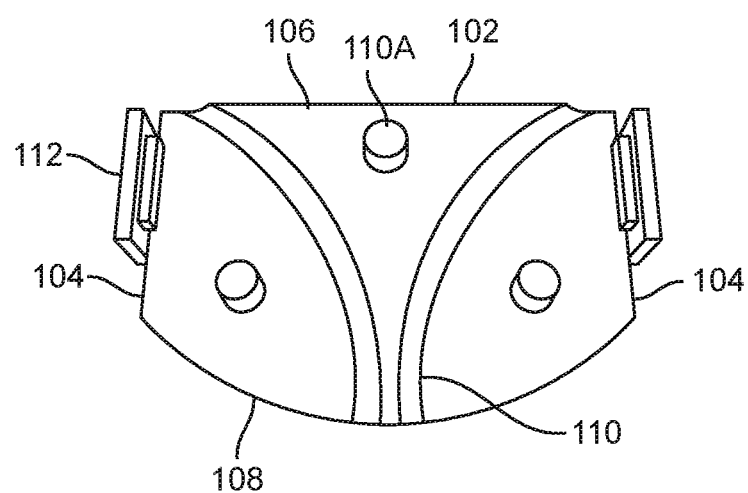
FIG. 1 shows an example of a bottom plate.
Figure 2:
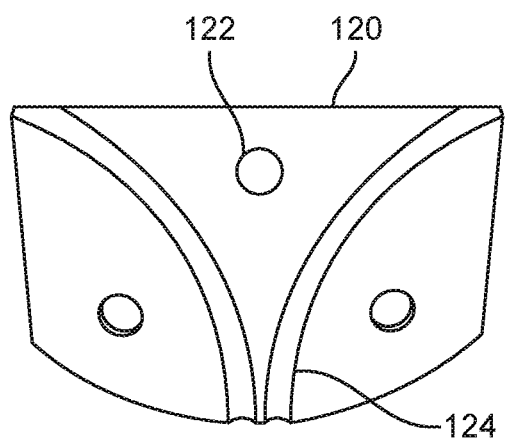
FIG. 2 shows an example of a top plate.
Figure 3:
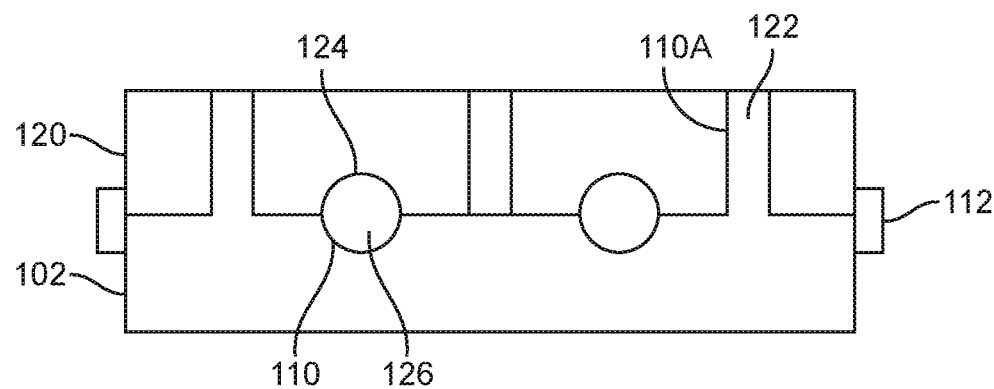
FIG. 3 shows the top and bottom plates from FIGS. 1-2 engaged with one another.

FIGS. 1-3 illustrate one example of a catheter management device.

FIG. 1 illustrates an example of a bottom plate 102 that may be used in a catheter or guidewire management device. The bottom plate may be a flat planar plate of any shape. Here the plate has two linear lateral sides 104 and an arcuate distal edge 108 and a linear proximal edge 106. The linear proximal edge 106 may be facing the operator and the arcuate distal edge 108 may be facing the patient, or the opposite orientation may be used where the linear proximal edge faces toward the patient and the arcuate edge faces toward the operator. Any number of grooves 110 may be disposed in the upper surface of the bottom plate. Here, two arcuate grooves are included such that at one end of the plate, the grooves are adjacent one another and substantially parallel with one another, and at the opposite end of the plate, the grooves diverge away from one another. However, any groove configuration may be used such as linear grooves that are parallel with one another or transverse to one another. An arcuate groove 110 may provide a smooth curve that a catheter shaft or guidewire may navigate as it is being slidably advanced through the groove. One or more pins 110a, here three, extend up from the top surface of the bottom plate and serve as alignment pins when the bottom plate is aligned with holes in a top plate as will be discussed below. Although this is not intended to be limiting, and the pins may be disposed on the top plate and the holes on the bottom plate, or a combination of pins and holes may be on both plates. Additionally, on either lateral side, a wall 112 extends vertically away from the top surface of the plate. The walls serve as alignment elements to help align a top plate with the bottom plate 102 when the two plates are coupled together.

FIG. 2 illustrates an example of a top plate 120 which may be used with the bottom plate 102 in FIG. 1 to form a catheter or guidewire management device. Here, the top plate 120 is also a flat planar plate and has a shape that matches the bottom plate 102 shape such that when the two plates are stacked on top of one another, they form a uniform profile. However, this is not intended to be limiting, and any shape may be used. Optionally in any example, the shape may be compact enough to easily fit in an operator's hand for easy carrying and manipulation, or the device may rest on a surface. In this example, the top plate 120 includes alignment holes 122 which extend through the top plate and they are positioned to align with and cooperate with the alignment pins 110a in the bottom plate 102. Additionally, the grooves 124, here two, in the top plate also cooperate with the grooves 110 in the bottom plate 102 such that when opposite grooves are stacked on top of one another, they form one or more channels, here there are two channels. Each groove may be roughly half the diameter of a catheter shaft or a guidewire, although this is not intended to be limiting. In some examples the grooves may be less than half the diameter of the catheter shaft or guidewire and therefore when the two plates are coupled together they will capture the guidewire or catheter shaft in the resulting channel and due to the tight fit, this prevents axial movement of the catheter shaft or guidewire along the shaft. In other examples the groove may be larger than half the diameter of the guidewire or catheter shaft to allow slidable movement when the two plates are coupled together. In this example, the grooves are arcuate to match the grooves in the bottom plate, and similarly the grooves are adjacent one another at one end of the plate and substantially parallel with one another, and they diverge away from one another at the opposite end. The channel is sized to receive a guidewire or catheter shaft and hold it to prevent entanglement while still allowing an operator to slidably move or rotate the wire or shaft while in the management device, or when the plates in the management device are separated from one another.

The size and shape of the top 120 and bottom 102 plates may be any size or shape. Optionally in any example, the top and bottom plates may be sized and shaped to easily fit in an operator's hand for easy holding and manipulation. The top and bottom plates may be rigid, soft, flexible, resilient or have any desired combination of material properties. The top plate, bottom plate, or grooves may include a lining of material such as Teflon to provide a low friction surface against which the catheter or guidewire may easily slide and be rotated. Oil or other lubricants may also be coated onto the top plate, bottom plate, or grooves to facilitate sliding or rotation of the guidewire or catheter in the groove.

FIG. 3 shows the top plate 120 stacked on top of the bottom plate 102 so the two plates sit flush against one another. The alignment pins 110a of the bottom plate are received in the alignment apertures 122 of the top plate. The top plate may be lifted off of the bottom plate at any time to allow access to the guidewires or catheter shafts that may be disposed in the channel 126 formed where opposite grooves 110, 124 mate. Sidewall 112 helps align the top plate with the bottom plate and also may prevent unwanted lateral movement of the top plate relative to the bottom plane.

Figure 4:
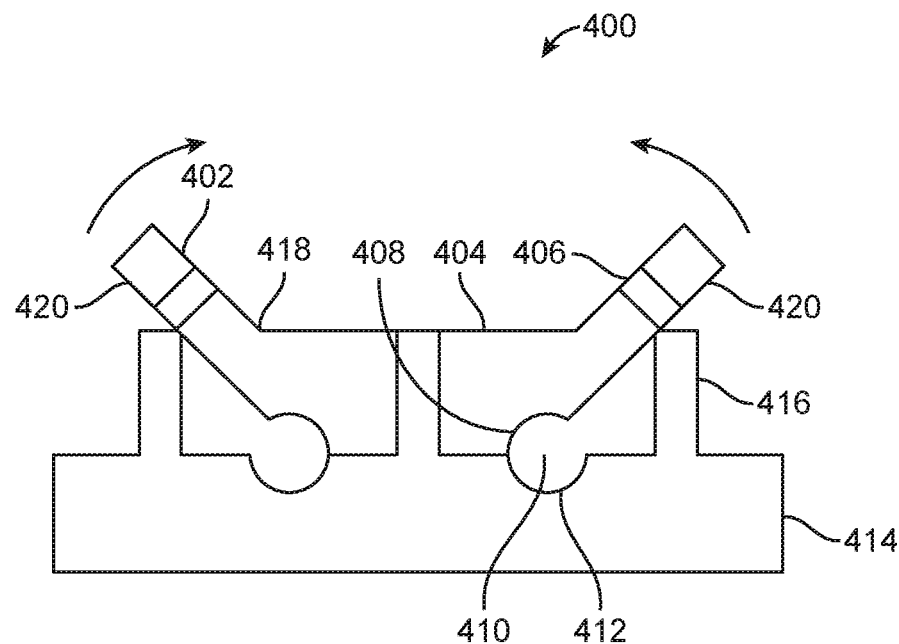
FIG. 4 shows a hinge element in the top plate.

FIG. 4 shows an example of a catheter or guidewire management device 400 having a top plate 404 coupled to a bottom plate 414. The top and bottom plates 404, 414 are similar to those described previously in FIGS. 1-3 above in that the bottom plate includes pins 416 for alignment with apertures 406 in the top plate. Additionally, the top and bottom plates 404, 414 also includes grooves 408, 413 that cooperate with one another to form channels 410 that receives a catheter shaft or guidewire. In this example, the top plate 404 includes a hinge or a hinge 418 formed as a result of the top plate being made of a flexible and resilient material in a middle section of the top plate between opposite lateral sides 420 of the top plate 404. Examples may include silicone, polyurethane etc. The hinge 418 allows either or both lateral sides 420 to be flexed and rotated up and away from the bottom plate 414 to expose the channel 410 formed by the mating grooves 408, 412 and this allows easy loading, unloading or other manipulation of a guidewire or catheter shaft in the channel 410. One lateral side 420 may be lifted while the other lateral side remains engaged with the lower plate, or both may be lifted concurrently or sequentially. Other aspects of the device 400 are generally the same as described with respect to FIGS. 1-3.

Figure 5A:
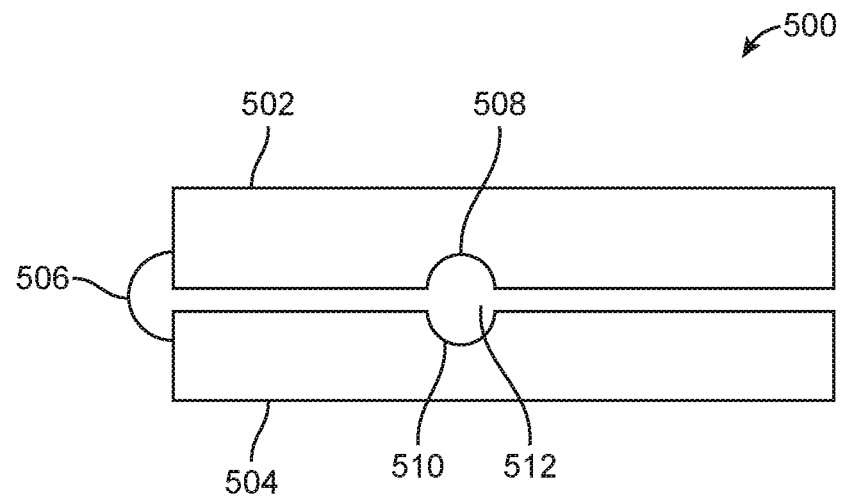
FIGS. 5A-5B show a top plate and bottom plate with a hinge on a lateral side.
Figure 5B:
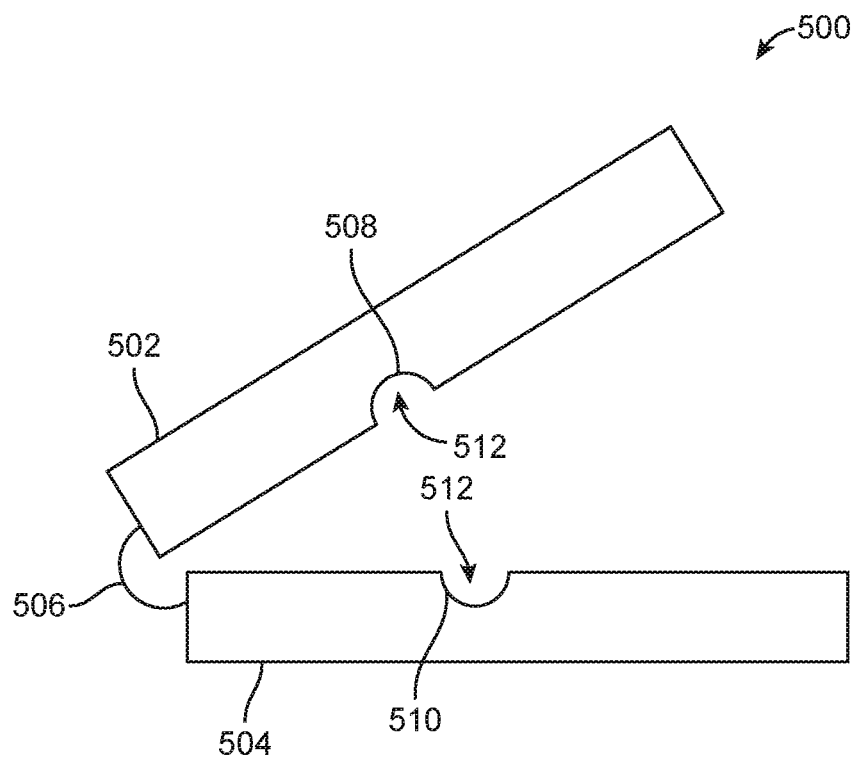

FIGS. 5A-5B illustrate another example of a catheter or guidewire management device 500 that is hinged. In FIG. 5A the top plate 502 is stacked on top of the bottom plate 504, and the top and bottom plates 502, 504 may include any of the features of the plates described previously (e.g. grooves, alignment pins, alignment holes, alignment walls, etc.). Here, the top plate 502 is a flat planar plate with a groove 508 disposed on an inner surface of the plate. The bottom plate 504 is also a flat planar plate with a cooperating groove 510 on an inner surface of the plate. When the upper and lower plates 502, 504 are apposed with one another, the two grooves 508, 510 cooperate with one another to form a channel 512 that is sized to receive a catheter or guidewire. The size of the channel 512 be may be slightly oversized relative to the catheter or guidewire in order to allow slidable movement of the catheter or guidewire in the channel, or the size may be small enough to pinch the catheter or guidewire and prevent axial movement. A hinge 506 is disposed on a lateral side of the device coupled to the top and bottom plates 502, 504. The hinge may be any type of hinge and allows the two plates to pivot relative to one another.

FIG. 5B shows the device 500 partially opened where the hinged ends of the top and bottom plates remain adjacent one another while the opposite ends of the plates rotate away from one another to allow access to a catheter or guidewire when disposed in the channel 512 formed by the opposing grooves 508, 510. Here, a single channel 512 is illustrated however this is not intended to be limiting and multiple grooves may be included to form multiple channels. Also, as discussed, any of the other features in FIGS. 1-3 may be used in conjunction with or substituted for any of the features in FIGS. 5A-5B, for example the alignment pins and holes that receive the pins may also be included in device 500.

Figure 6A:
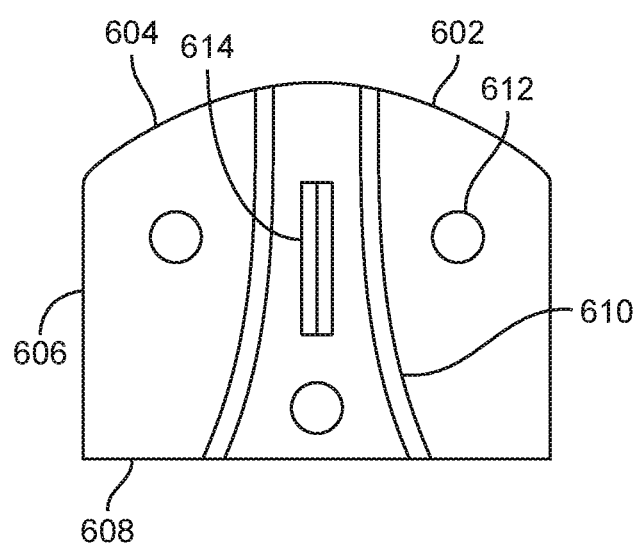
FIGS. 6A-6C illustrate an example of top plate and a bottom plate with a central hinge element.
Figure 6B:
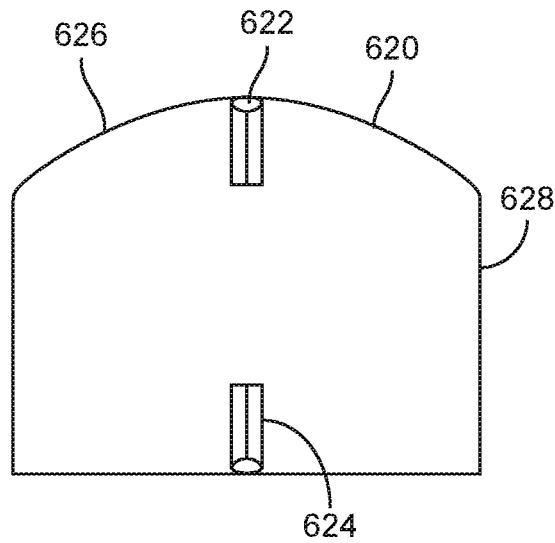
Figure 6C:
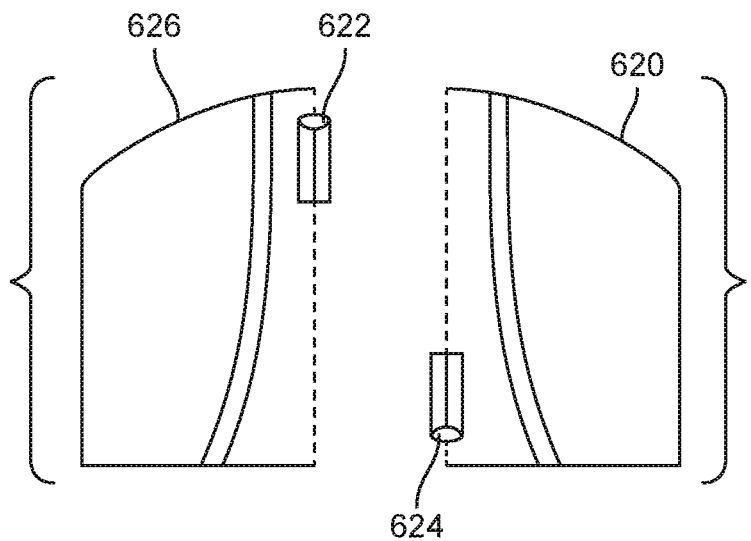

FIGS. 6A-6C illustrate another example of a catheter or guidewire management device that is hinged.

FIG. 6A shows the bottom plate 602 with two grooves 610, alignment features 612 such as pins, or apertures for receiving pins, and hinge element 614 in a central portion of the bottom plate. One end 604 of the bottom plate may be curved while the opposite end 608 may be straight. The left and right lateral sides 606 may be straight edges. The grooves 610 may be linear and substantially parallel on one end of the bottom plate and the grooves 610 may diverge away from one another in an arcuate path on the opposite end of the plate. The hinge in this example 614 is a tube that can interdigitate with tubes on the upper plate and then a pin may be inserted through the channel in the tubes to form the hinge which allows independent opening of one half of the upper plate relative to the other half of the upper plate.

FIG. 6B shows the cooperating top plate 620 that mates with the bottom plate 602 and that also has a hinge elements 622, 624 along a midline of the upper plate 620 which in this case is two separate plates that are independently movable relative to one another when coupled with hinge 614 on the bottom plate. The upper plate may have a shape that mirrors that of the lower plate and may also include apertures for receiving alignment pins in the lower plate, or the upper plate may have pins that are received in apertures in the lower plate. Also, the upper plate may have grooves which cooperate with the grooves in the lower plate to form channels for receiving a guidewire or catheter. The alignment pins or holes and grooves are not illustrated for convenience. The hinge 622, 624 are tubular members axially separated from one another so that the hinge 614 from the lower plate may be disposed in the gap between the two upper tubular members and when aligned, a pin may be inserted into the central channel of all the tubes thereby forming the hinge similar to a traditional door hinge. Because the upper plate is split into two halves, each half is therefore configured to be rotated up and down relative to the other half of the top plate independently from one another.

FIG. 6C shows the upper plate 620 in FIG. 6B but with the two halves separated from one another. Also, FIG. 6C shows the two grooves in the top plate that cooperate with the two grooves in the lower plate of FIG. 6A to form the channels for the catheter or guidewire. Here upper plate 620 includes a left and right lateral side, each with a tubular hinge element 622, 624, and that either left, or right or both lateral sides may then be rotated up and toward the midline of the top plate to expose the grooves/channels in the device along with any guidewires or catheters which may be disposed in the channels. Either side may be opened first while the other side remains closed, or both may be opened, or both may be opened concurrently.

In any example of a guidewire or catheter management device, it may be desirable to provide a bracket or other element to facilitate holding or manipulation of the management device by an operator.

Figure 7A:
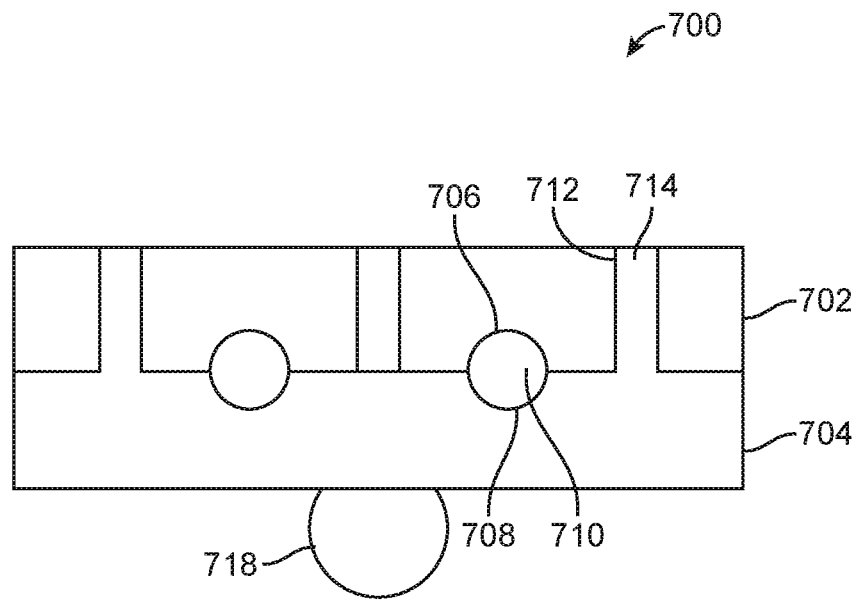
FIG. 7A-7B illustrate examples of grasping elements.

FIG. 7A shows a catheter or guidewire management device 700 with a top plate 702 and a bottom plate 704 which may be any of the examples disclosed herein, and they may be hingedly coupled together using any of the hinges disclosed herein. The device 700 also includes an annular ring 718 on the bottom plate. Other aspects of the device 700 are similar to other examples previously described above. For example, both upper and lower plates 702, 704 include grooves 706, 708 that when opposed form channels 710 for holding a catheter or guidewire. Additionally, the top plate and bottom plate may have alignment pins or holes for receiving the pins to ensure alignment of the top and bottom plates. The annular ring 718 is coupled to the bottom surface of the bottom plate. The ring is sized so that an operator can insert a finger into the annular ring 718 and this helps hold the management device or allows the management device to be easily manipulated. For example, the management device may be rotatable relative to the ring holder thus the operator can still maintain a grasp on the device while rotating the two plates.

Figure 7B:
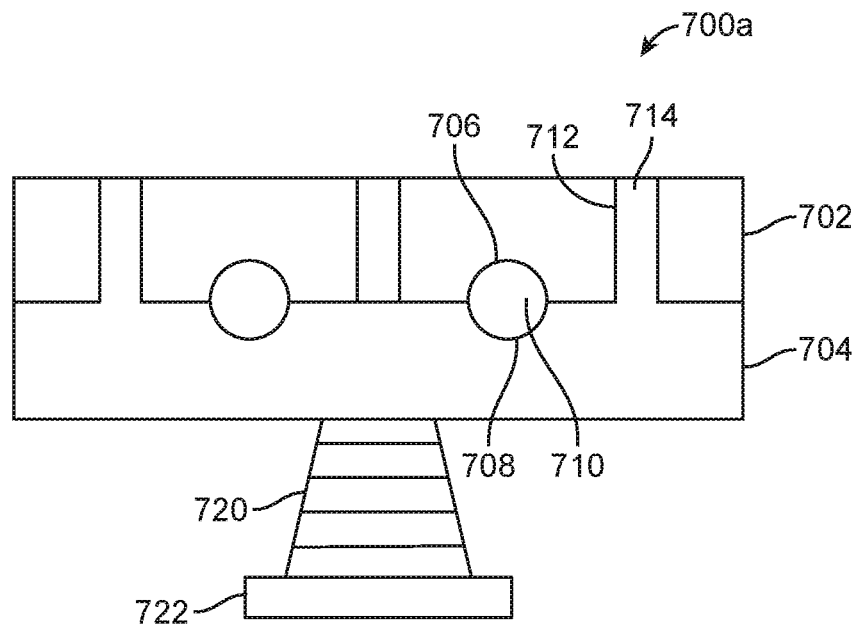

FIG. 7B shows another example of a guidewire or catheter management device 700a that is essentially the same as the example in FIG. 7A but with the major difference being that instead of the annular ring 718, this device 700a includes an expandable and collapsible holding element 720. The holding element 720 is an accordion type element that is coupled to the bottom surface of the bottom plate 704. In use the accordion may be extended and when not in use, the accordion may be collapsed onto a smaller configuration. The accordion section may be disposed between two fingers in the operator's hand to allow the operator to hold or otherwise manipulate the management device 700a. A larger diameter flanged region 722 provides a stop element and prevents the fingers from sliding past the flanged region. Other aspects of the device 700a are generally the same as previously described in FIG. 7A. For example, the top and bottom plates 702, 704 may both include grooves 706, 708 that when apposed with one another form channels 710 for holding a catheter or guidewire. The pins 712 and holes for receiving the pins 714 may be disposed on either the top or bottom plates, and any hinge may be used to couple the two plates together, or no hinge may be used at all.

In any example a bracket or other fixture (not illustrated) may be coupled to the bottom or top plate to allow the management device to be coupled, clipped, or otherwise attached to a surface such as a procedure table.

In any example, the top and/or bottom plates may include color coding, labeling, icons, or other indicia to allow an operator to easily identify which catheter or guidewire is disposed in which groove.

FIGS. 8-13 show an example of another catheter or guidewire management device 800.

Figure 8:
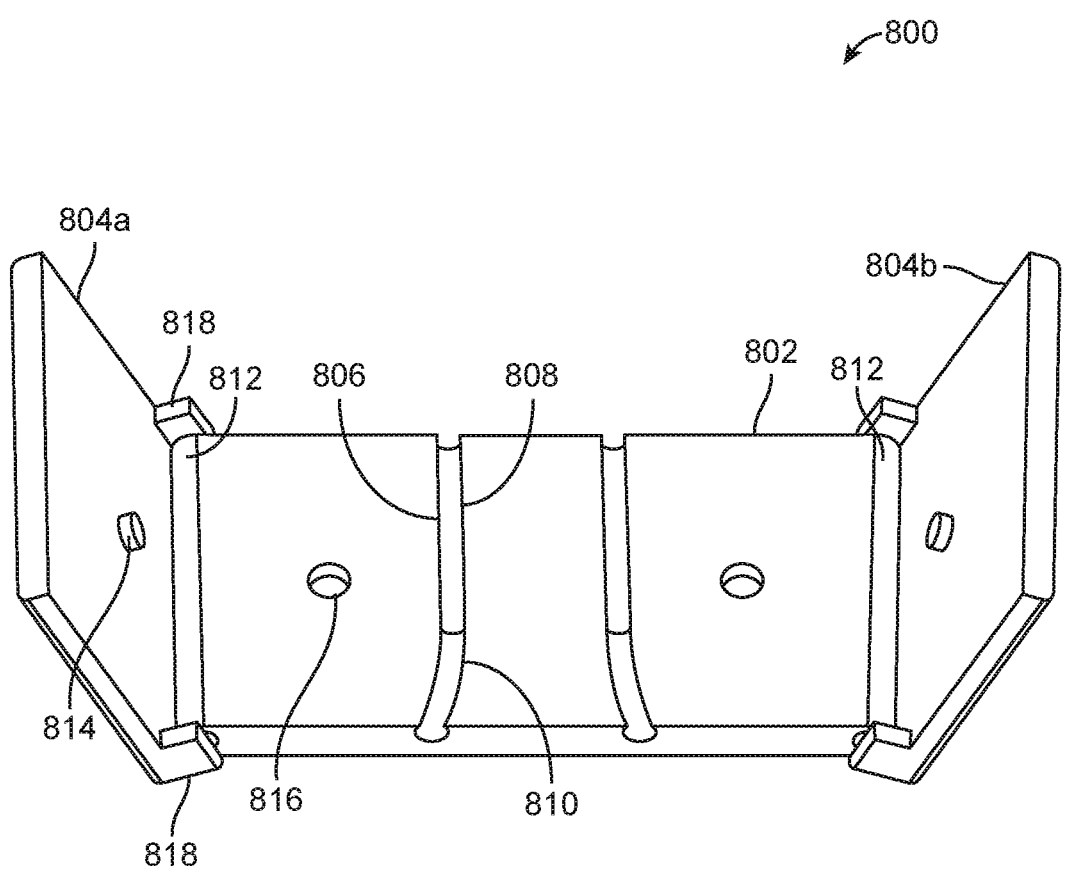
FIGS. 8-13 show another example of a catheter management device.

FIG. 8 shows the management device 800 having a lower plate 802 and an upper plate that is formed from two separate upper plate portions 804a, 804b that pivot independently of one another. The upper plate portions 804a, 804b are pivotably coupled to the lower plate 802 via hinges 812. The lower plate includes two grooves 806 that are sized to hold a guidewire or catheter. The grooves 806 on one end of the lower plate are substantially parallel 808 to one another, while on the opposite end the groves flare 810 away from one another. The flared end may face the patient and the parallel grooved end may face the operator, or the opposite orientation may be used where the flared end may face the patient and the parallel grooved end may face the operator.

Here, there are two grooves in the bottom plate, and they may be any size but may be greater than 180 degrees of the circumference of the catheter or guidewire but less than 360 degrees. Thus, when a catheter or guidewire is disposed in the groove 806, a portion is raised above the upper surface lower plate. When the upper plate is closed against the lower plate, the upper and lower plates sandwich the catheter or guidewire holding the catheter or guidewire in position and preventing axial movement. Here, the grooves 808 that are substantially parallel to one another may be distal of the operator and closest to the patient so that the catheters or guidewires enter the patient in substantially parallel direction. The flared grooves 810 may be closest to the operator and prevent entanglement and allow easy separation and identification of the proximal ends of the catheters or guidewires. The lower plate 802 includes alignment holes 816 which are sized to receive the pins 814 protruding out of the lower surface of the top plate 804a, 804b. The position of the pins and alignment holes may also be reversed or used in any permutation or combination.

The upper plates 804a, 804b are substantially flat and planar plates with two arms 818 that extend from opposite sides of the upper plates 804a, 804b on one end of the upper plates 804a, 804b. These arms 818 receive a pin that protrudes from the sides of the lower plate allowing the upper plates 804a, 804b to pivot open and closed. When closing, the upper plates pivot inward toward the midline of the lower plate and toward one another, and when opening the upper plates pivot outward away from one another and away from the midline. Both upper plates 804a, 804b are open in FIG. 8.

Figure 9:
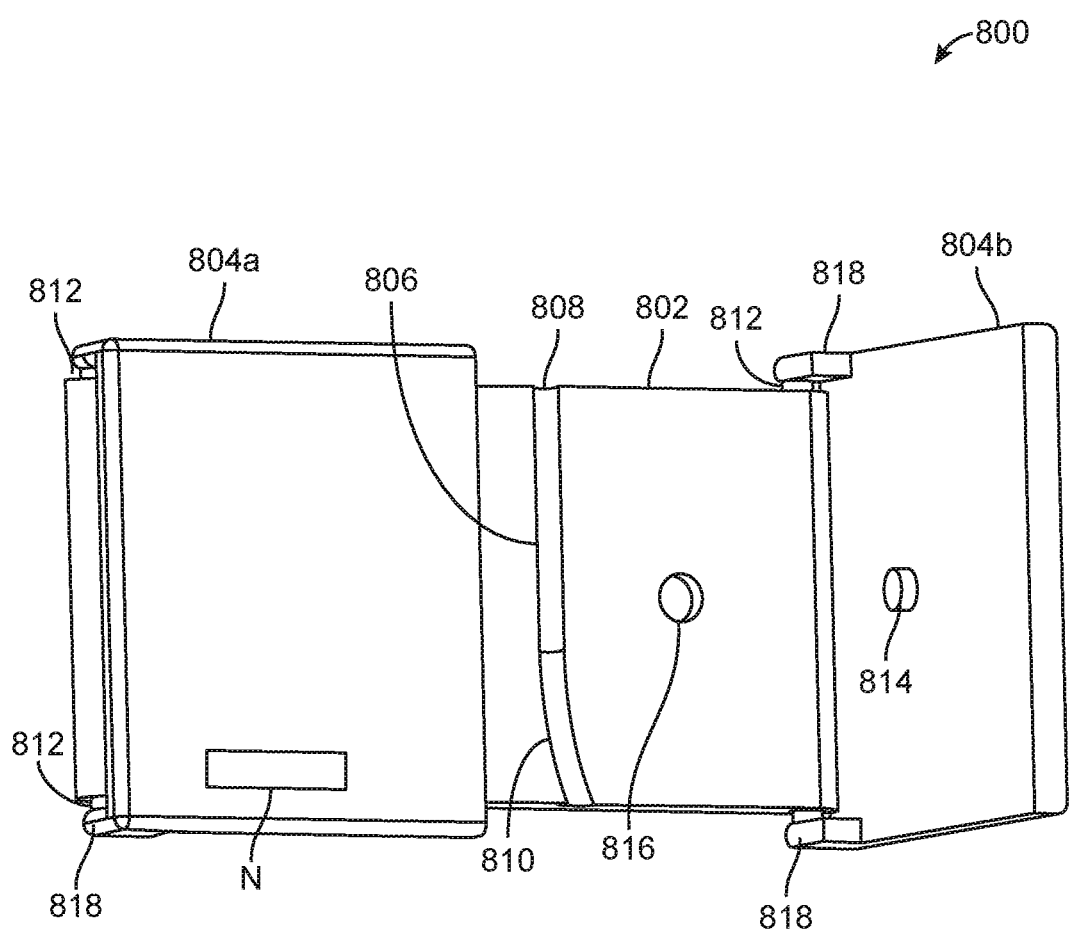

FIG. 9 shows the device 800 seen in FIG. 8, but this time with the right upper plate 804b open, and the left upper plate 804a closed thereby obstructing view of the one of the grooves in the lower plate while the other is exposed. Other aspects of FIG. 9 are generally the same as disclosed with respect to FIG. 8. FIG. 9 also shows that any marking or indicia N may be applied to any portion of the device 800 in order to help an operator identify catheters or guidewires disposed in the grooves.

Figure 10:
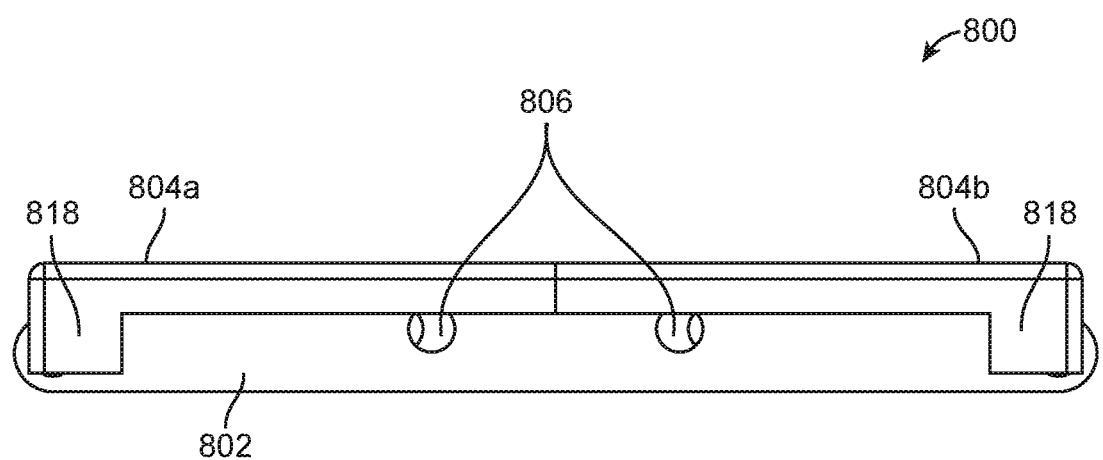

FIG. 10 shows a side view of the catheter or guidewire management device 800 with both upper plates closed against the lower plate. The view shows the grooves exiting the end of the device in a generally parallel direction relative to one another. Both upper plate portions 804a, 804b are closed and abut with the lower plate 802. Other aspects of FIG. 10 are substantially the same as in FIG. 9.

Figure 11:
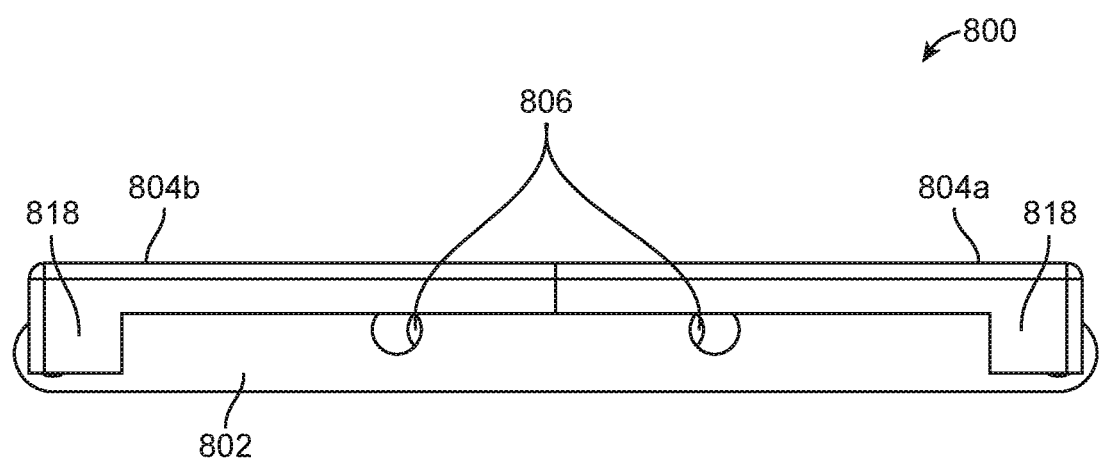

FIG. 11 shows the same device 800 as in FIG. 10 but is a side view of the device from the end opposite the end seen in FIG. 10. Thus, in this view the grooves 806 exit the device and flare away from one another. Other aspects of the device 800 in FIG. 11 are generally the same as in FIG. 9 above.

Figure 12:
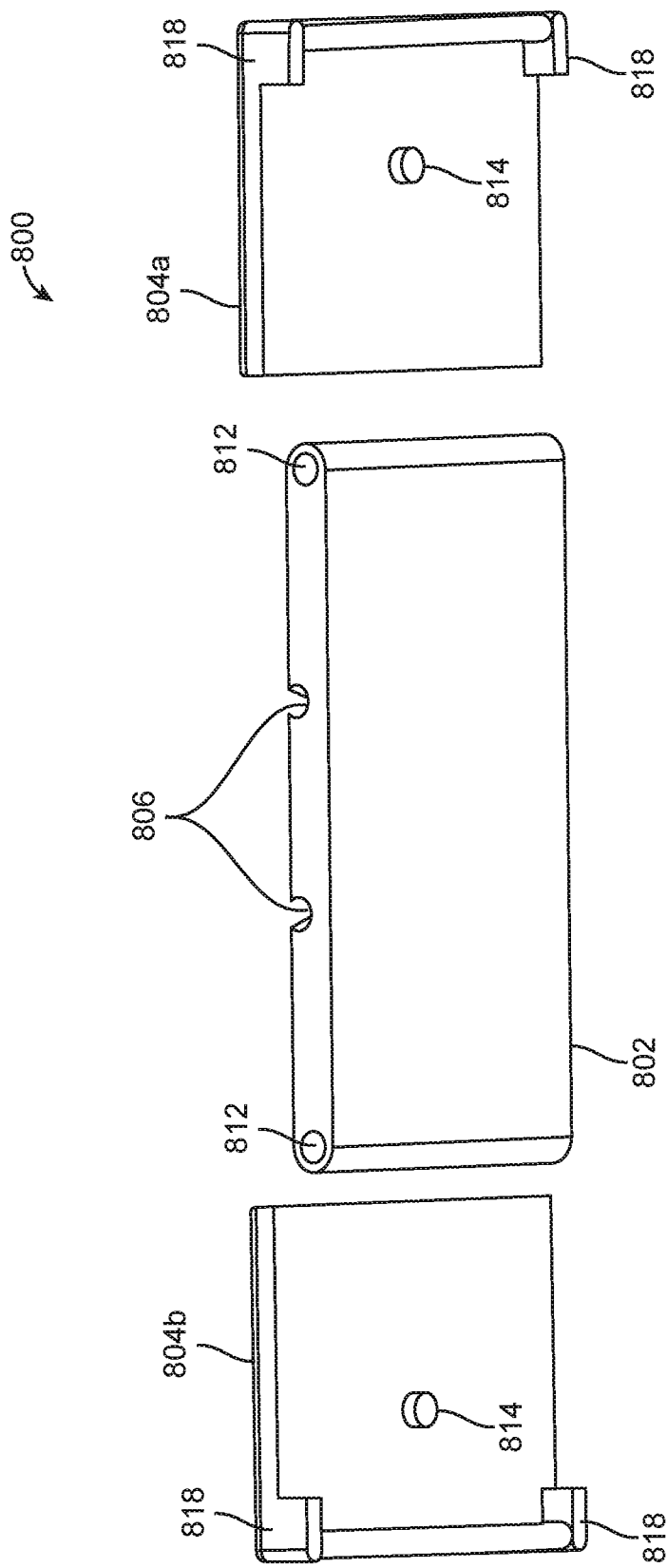

FIG. 12 shows an exploded view of the catheter or guidewire management device 800 shown in FIGS. 8-11 above.

Figure 13:
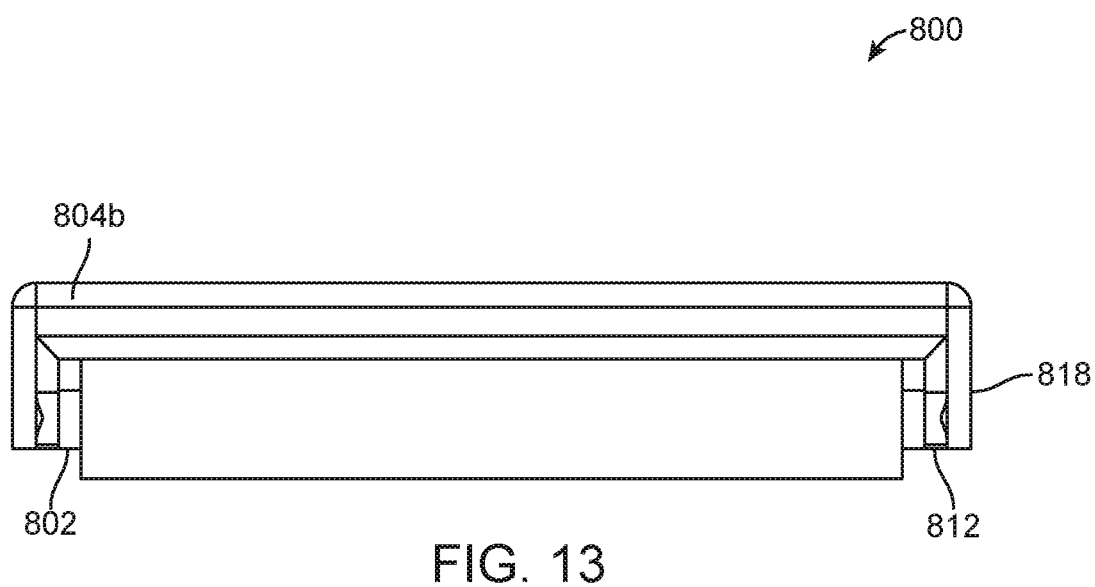

FIG. 13 shows an end view of the catheter or guidewire management device 800 from a lateral end of the device and shows the upper plate 804b closed and disposed against the lower plate 802. Other aspects of FIG. 13 are substantially the same as shown in FIGS. 8011 above.

NOTES AND EXAMPLES

The following, non-limiting examples, detail certain aspects of the present subject matter to solve the challenges and provide the benefits discussed herein, among others.

Example 1 is a device for management of an elongate shaft, the device comprising: an upper plate; and a lower plate having at least one lower groove disposed therein, the at least one lower groove in the lower plate sized to receive the elongate shaft, wherein the upper plate is releasably coupled to the lower plate and wherein the elongate shaft is captured between the upper plate and the lower plate.

Example 2 is the device of Example 1, wherein the upper plate further comprises at least one upper groove disposed therein, the at least one upper groove sized to receive the elongate shaft, and wherein the at least one lower groove in the lower plate cooperates with the at least one upper groove in the upper plate to form a channel configured to hold the elongate shaft.

Example 3 is the device of any of Examples 1-2, wherein the elongate shaft is constrained from slidable and rotational movement in the channel when the upper plate is apposed with the lower plate.

Example 4 is the device of any of Examples 1-3, wherein the at least one groove in the upper plate or the lower plate is arcuate.

Example 5 is the device of any of Examples 1-4, further comprising a hinge coupled to the upper and lower plates, wherein the hinge allows the upper plate to be rotated away from the lower plate, thereby allowing access to the at least one lower groove in the lower plate.

Example 6 is the device of any of Examples 1-5, wherein the hinge is coupled to a side of the upper plate and a side of the lower plate.

Example 7 is the device of any of Examples 1-6, wherein the upper plate comprises a first half and a second half, the first and second halves coupled together with a hinge, and wherein the first half is independently rotatable relative to the second half.

Example 8 is the device of any of Examples 1-7, wherein the at least one lower groove in the lower plate comprises a first lower groove disposed therein and a second lower groove disposed therein, wherein the first lower groove is sized to receive the elongate shaft, and wherein the second lower groove is sized to receive a second elongate shaft, and wherein the first half of the upper plate rotates independently of the second half of the upper plate to expose the first lower groove while the second lower groove remains covered by the second half of the upper plate, and wherein the second half of the upper plate rotates independently of the first half of the upper plate to expose the second lower groove while the first lower groove remains covered by the first half of the upper plate.

Example 9 is the device of any of Examples 1-8, wherein the first half of the upper plate rotates inward toward the second half of the upper plate, and wherein the second half of the upper plates rotates inward toward the first half of the upper plate.

Example 10 is the device of any of Examples 1-9, wherein the first half of the upper plate rotates outwardly away from the second half of the upper plate and, wherein the second half of the upper plate rotates outwardly away from the first half of the upper plate.

Example 11 is the device of any of Examples 1-10, further comprising a grasping element coupled to a lower surface of the lower plate, wherein the grasping element is sized and shaped to facilitate grasping and manipulation of the device with an operator's hand.

Example 12 is the device of any of Examples 1-11, wherein the grasping element comprises a ring configured to receive an operator's finger.

Example 13 is the device of any of Examples 1-12, wherein the grasping element is expandable and collapsible between a collapsed configuration and an expanded configuration.

Example 14 is the device of any of Examples 1-13, wherein the lower plate is rotatable relative to the grasping element.

Example 15 is the device of any of Examples 1-14, further comprising one or more pins, wherein the one or more pins are coupled to the upper plate or the lower plate, and wherein the other of the upper plate or the lower plate further comprises one or more apertures for receiving the one or more pins to align the upper and lower plates with one another.

Example 16 is the device of any of Examples 1-15, further comprising a side wall extending from a side of the lower plate, the side wall providing a stop for facilitating alignment of the upper plate with the lower plate and for preventing lateral movement of the upper plate relative to the lower plate.

Example 17 is the device of any of Examples 1-16, wherein the upper plate is formed from a resilient material which permits either a first lateral portion of the upper plate or a second lateral portion of the upper plate opposite the first lateral portion to flex upward and away from the lower plate.

Example 18 is the device of any of Examples 1-17, further comprising indicia on the upper plate or the lower plate to facilitate identification of the elongate shaft disposed in the at least one groove of the lower plate.

Example 19 is the device of any of Examples 1-18, wherein the elongate shaft comprises a guidewire or a catheter shaft.

Example 20 is the device of any of Examples 1-19, wherein the upper plate comprises a first portion and a second portion, wherein the first portion is hingedly coupled with a first end of the lower plate, and the second portion is hingedly coupled with a second end of the lower plate opposite the first end, and wherein the first and second portions open independently away from one another to expose the at least one lower groove in the lower plate.

Example 21 is the device of any of Examples 1-20, wherein the at least one lower groove comprises a first lower groove and a second lower groove disposed in the lower plate, wherein the first and second lower grooves extend from a first edge of the lower plate to a second edge of the lower plate opposite the first edge, and wherein adjacent the first edge the first and second lower grooves are substantially parallel with one another, and wherein adjacent the second edge the first and second lower grooves flare away from one another.

Example 22 is a method for managing an elongate shaft, the method comprising: providing an elongate shaft management device comprising an upper plate and a lower plate; disposing the elongate shaft in a groove in the lower plate; and apposing the upper plate against the lower plate thereby capturing and constraining movement of the elongate shaft therebetween.

Example 23 is the method of Example 22, wherein the upper plate comprises a groove disposed therein, and wherein the groove in the upper plate cooperates with the groove in the lower plate to form a channel for capturing the elongate shaft when the upper plate is apposed with the lower plate.

Example 24 is the method of any of Examples 22-23, further comprising separating the upper plate from the lower plate and manipulating the elongate shaft.

Example 25 is the method of any of Examples 22-24, wherein separating the upper plate from the lower plate comprises hingedly opening the upper plate relative to the lower plate to provide access to the elongate shaft disposed in the groove of the lower plate.

Example 26 is the method of any of Examples 22-25, wherein separating the upper plate from the lower plate comprises opening a lateral end of the upper plate away from a lateral end of the lower plate.

Example 27 is the method of any of Examples 22-26, wherein the separating the upper plate from the lower plate comprises opening a first side of the upper plate away from the lower plate and towards a center of the lower plate.

Example 28 is the method of any of Examples 22-27, wherein the upper plate comprises a first portion and a second portion, wherein the first portion is hingedly coupled with a first end of the lower plate, and the second portion is hingedly coupled with a second end of the lower plate opposite the first end, and wherein separating the upper plate from the lower plate comprises independently opening the first portion away from the lower plate or independently opening the second portion away from the lower plate, and exposing the groove in the lower plate.

Example 29 is the method of any of Examples 22-28, further comprising disposing a second elongate shaft in a second groove in the lower plate.

Example 30 is the method of any of Examples 22-29, wherein the elongate shaft comprises a guidewire or a catheter shaft.

Example 31 is the method of any of Examples 22-30, wherein the lower plate comprises a side wall extending therefrom, and wherein apposing the upper plate against the lower plate comprises aligning the upper plate with the side wall. Example 32 is the method of any of Examples 22-31, wherein apposing the upper plate against the lower plate comprises aligning the upper plate with the lower plate by inserting pins extending from the lower plate into cooperating apertures disposed in the upper plate.

Example 33 is the method of any of Examples 22-32, further comprising grasping a grasping element coupled to a lower surface of the lower plate.

Example 34 is the method of any of Examples 22-33, further comprising rotating the management device relative to the grasping element.

Example 35 is the method of any of Examples 22-34, further comprising expanding or collapsing the grasping element between a collapsed configuration and an expanded configuration to provide a surface for grasping.

Example 36 is the method of any of Examples 22-35, wherein grasping the grasping element comprises inserting a finger into a ring coupled to the lower plate.

In Example 37, the apparatuses or methods of any one or any combination of Examples 1-36 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A guidewire or catheter shaft management device, the device comprising:
   an upper plate comprising at least one upper groove disposed therein, the at least one upper groove sized to receive a guidewire or catheter shaft;
   a lower plate comprising at least one lower groove disposed therein, the at least one lower groove in the lower plate sized to receive the guidewire or catheter;
   wherein the upper plate is detachably coupled to the lower plate and wherein the guidewire or catheter is capturable between the upper plate and the lower plate, and wherein the at least one lower groove in the lower plate cooperates with the at least one upper groove in the upper plate to form a channel configured to hold the guidewire or catheter shaft, the upper and lower plates having alignment pins and apertures with each alignment pin received in a corresponding aperture when the upper plate is coupled to the lower plate; and wherein the upper plate and the lower plate are configured such that the upper plate can be completely detached from the lower plate to allow access to a guidewire or catheter shaft received in a said channel, wherein the at least one lower groove comprises a first lower groove and a second lower groove disposed in the lower plate, wherein the first and second lower grooves extend from a first edge of the lower plate to a second edge of the lower plate opposite the first edge, and wherein adjacent the first edge the first and second lower grooves are substantially parallel with one another, and wherein adjacent the second edge the first and second lower grooves flare away from one another in respective curved arcs that diverge away from one another.

2. The device of claim 1, wherein the at least one upper groove comprises a first upper groove and a second upper groove disposed in the upper plate, wherein the first and second upper grooves extend from a first edge of the upper plate to a second edge of the upper plate opposite the first edge, and wherein adjacent the first edge the first and second upper grooves are substantially parallel with one another, and wherein adjacent the second edge the first and second upper grooves flare away from one another in respective curved arcs that diverge away from one another.

3. The device of claim 2, wherein;
the alignment pins comprise an alignment pin configured on a first region of the lower plate, the first region of the lower plate being bounded by the second edge of the lower plate, the first lower groove, and the second lower groove; and
the apertures comprise an aperture configured on a second region of the upper plate, the second region of the upper plate being bounded by the second edge of the upper plate, the first upper groove, and the second upper groove,
wherein when the upper plate is coupled to the lower plate the alignment pin configured on the first region of the lower plate is received in the aperture configured on the second region of the upper plate.

4. The device of claim 1, further comprising a grasping element coupled to the lower plate, the grasping element sized and shaped to facilitate grasping and manipulation of the device with an operator's hand.

5. The device of claim 1, further comprising a side wall extending from a side of the lower plate, the side wall providing a stop for facilitating alignment of the upper plate with the lower plate and for preventing lateral movement of the upper plate relative to the lower plate.

6. The device of claim 1, further comprising indicia on the upper plate or the lower plate to facilitate identification of the guidewire or catheter shaft disposed in the channel.

7. A method for managing a guidewire or catheter shaft, the method comprising:
providing a guidewire or catheter shaft management device, the device comprising:
an upper plate comprising at least one upper groove disposed therein, the at least one upper groove sized to receive a guidewire or catheter shaft;
a lower plate comprising at least one lower groove disposed therein, the at least one lower groove in the lower plate sized to receive the guidewire or catheter;
wherein the upper plate is detachably coupled to the lower plate and wherein the guidewire or catheter is capturable between the upper plate and the lower plate, and wherein the at least one lower groove in the lower plate cooperates with the at least one upper groove in the upper plate to form a channel configured to hold the guidewire or catheter shaft, the upper and lower plates having alignment pins and apertures with each alignment pin received in a corresponding aperture when the upper plate is coupled to the lower plate; and
wherein the upper plate and the lower plate are configured such that the upper plate can be completely detached from the lower plate to allow access to a guidewire or catheter shaft received in a said channel;
disposing the guidewire or catheter shaft in the at least one lower groove in the lower plate; and
apposing the upper plate against the lower plate thereby capturing and constraining movement of the guidewire or catheter shaft therebetween,
wherein the at least one lower groove comprises a first lower groove and a second lower groove disposed in the lower plate, wherein the first and second lower grooves extend from a first edge of the lower plate to a second edge of the lower plate opposite the first edge, and wherein adjacent the first edge the first and second lower grooves are substantially parallel with one another, and wherein adjacent the second edge the first and second lower grooves flare away from one another in respective curved arcs that diverge away from one another.

8. The device of claim 1, wherein the grooves are either:
less than half a diameter of the catheter shaft or guidewire to capture the guidewire or catheter shaft in the channel to prevent axial movement of the catheter shaft or guidewire; or
larger than half the diameter of the guidewire or catheter shaft to allow slidable movement when the two plates are coupled together.

9. The device of claim 1, wherein the at least one upper groove in the upper plate, or the at least one lower groove in the lower plate is arcuate.

10. The device of claim 1, wherein the lower plate is a flat planar plate having two linear lateral sides and an arcuate distal edge and a linear proximal edge, wherein the at least one lower groove comprises two arcuate grooves, wherein at one end of the plate, the grooves are adjacent one another and substantially parallel with one another, and at an opposite end of the plate, the grooves diverge away from one another;
wherein on either lateral side, a wall extends vertically away from a top surface of the lower plate, the walls serving as alignment elements to help align the upper plate with the lower plate when the two plates are coupled together; and
wherein the upper plate is also a flat planar plate and has a shape that matches the lower plate shape, wherein each channel is sized to receive a guidewire or catheter shaft and hold it to prevent entanglement while still allowing an operator to slidably move or rotate the guidewire or catheter shaft while in the management device or when the plates in the management device are detached from one another.

11. The device of claim 1, wherein the upper and lower plates are sized and shaped to fit in an operator's hand for holding and manipulation.

12. The device of claim 1, wherein the upper and lower plates are rigid, soft, flexible or resilient.

13. The device of claim 1, wherein the upper plate, the lower plate, or the grooves include a lining of material to provide a low friction surface against which the catheter shaft or guidewire may slide and be rotated.

14. The device of claim 4, wherein the grasping element comprises an annular ring coupled to a bottom surface of the lower plate, the ring being sized so that an operator can insert a finger into the annular ring.

15. The device of claim 4, wherein the grasping element comprises an expandable and collapsible holding element.

* * * * *